(12) United States Patent
Mangat et al.

(10) Patent No.: US 9,421,280 B2
(45) Date of Patent: Aug. 23, 2016

(54) REAL TIME IMAGING DURING SOLID ORGAN TRANSPLANT

(71) Applicant: Novadaq Technologies Inc., Mississauga (CA)

(72) Inventors: Gurpreet Mangat, Markham (CA); Lukasz Brzozowski, Toronto (CA); Richard L. Croft, Oakville (CA)

(73) Assignee: Novadaq Technologies Inc., Mississauga (CA)

( * ) Notice: Subject to any disclaimer, the term of this patent is extended or adjusted under 35 U.S.C. 154(b) by 212 days.

(21) Appl. No.: 14/177,045

(22) Filed: Feb. 10, 2014

(65) Prior Publication Data

US 2014/0308210 A1    Oct. 16, 2014

Related U.S. Application Data

(60) Division of application No. 11/912,877, filed as application No. PCT/US2006/016089 on Apr. 26, 2006, now Pat. No. 8,647,605, which is a continuation of application No. 11/114,501, filed on Apr. 26, 2005, now abandoned.

(51) Int. Cl.
*A61B 10/00* (2006.01)
*A61B 5/00* (2006.01)
*A61B 8/00* (2006.01)
*A61K 49/00* (2006.01)

(52) U.S. Cl.
CPC ......... *A61K 49/0045* (2013.01); *A61K 49/0019* (2013.01); *A61K 49/0032* (2013.01); *A61K 49/0034* (2013.01); *A61K 49/0041* (2013.01); *A61K 49/0043* (2013.01)

(58) Field of Classification Search
CPC .............. A61K 49/00; A61K 49/0056; A61K 49/0034; A61K 49/0019; A61K 49/0032; A61K 49/0041; A61K 49/0043; A61K 49/0045; A61K 49/0021; A61K 49/0002; A61K 49/001; A61K 49/0013; A61K 49/0017; A61K 49/0023; A61K 49/0026; A61K 49/0028; A61K 49/003; A61K 49/0039; A61K 49/005; A61K 49/006
USPC ............ 424/1.11, 1.65, 9.1, 9.2, 9.6; 600/431
See application file for complete search history.

(56) References Cited

U.S. PATENT DOCUMENTS

| | | |
|---|---|---|
| 4,394,199 A | 7/1983 | Barnhard, IV et al. |
| 4,619,249 A | 10/1986 | Landry |
| 4,995,396 A | 2/1991 | Inaba et al. |
| 4,995,398 A | 2/1991 | Turnidge |
| 5,115,137 A | 5/1992 | Andersson-Engels et al. |
| 5,178,616 A | 1/1993 | Uemiya et al. |
| 5,279,298 A | 1/1994 | Flower |
| 5,318,869 A | 6/1994 | Hashimoto et al. |
| 5,375,603 A | 12/1994 | Feiler |
| 5,394,199 A | 2/1995 | Flower |
| 5,437,274 A | 8/1995 | Khoobehi et al. |
| 5,438,989 A | 8/1995 | Hochman et al. |
| 5,453,448 A | 9/1995 | Narciso, Jr. |
| 5,465,718 A | 11/1995 | Hochman et al. |
| 5,507,287 A | 4/1996 | Palcic et al. |
| 5,699,798 A | 12/1997 | Hochman et al. |
| 5,785,965 A | 7/1998 | Pratt et al. |
| 5,845,639 A | 12/1998 | Hochman et al. |
| 5,851,181 A | 12/1998 | Talmor |
| 5,865,754 A | 2/1999 | Sevick-Muraca et al. |
| 5,927,284 A | 7/1999 | Borst et al. |
| 5,951,980 A | 9/1999 | Collen |
| 5,956,435 A | 9/1999 | Buzug et al. |
| 6,032,070 A | 2/2000 | Flock et al. |
| 6,081,612 A | 6/2000 | Gutkowicz-Krusin et al. |
| 6,122,042 A | 9/2000 | Wunderman et al. |
| 6,149,671 A | 11/2000 | Nordquist et al. |
| 6,179,421 B1 | 1/2001 | Pang |
| 6,196,226 B1 | 3/2001 | Hochman et al. |
| 6,233,480 B1 | 5/2001 | Hochman et al. |
| 6,241,672 B1 | 6/2001 | Hochman et al. |
| 6,246,901 B1 | 6/2001 | Benaron |
| 6,272,374 B1 | 8/2001 | Flock et al. |
| 6,280,386 B1 | 8/2001 | Alfano et al. |
| 6,293,911 B1 | 9/2001 | Imasizumi et al. |
| 6,335,429 B1 | 1/2002 | Cai et al. |
| 6,351,663 B1 | 2/2002 | Flower et al. |
| 6,353,750 B1 | 3/2002 | Kimura et al. |
| 6,443,976 B1 | 9/2002 | Flower et al. |
| 6,447,443 B1 | 9/2002 | Keogh et al. |
| 6,498,945 B1 | 12/2002 | Alfheim et al. |

(Continued)

FOREIGN PATENT DOCUMENTS

| | | |
|---|---|---|
| CA | 2212257 A1 | 8/1996 |
| CA | 2413033 A1 | 3/2000 |

(Continued)

OTHER PUBLICATIONS

Sekijima et al (Transplantation Proceedings, 2004, vol. 36, pp. 2188-2190).

(Continued)

*Primary Examiner* — D L Jones

(74) *Attorney, Agent, or Firm* — Morrison & Foerster LLP

(57) ABSTRACT

A method of determining the patency of a donor organ or at least one vessel to a donor organ in a donor subject includes administering a fluorescent dye to the donor subject, applying a sufficient amount of energy to the vessel such that the fluorescent dye fluoresces, obtaining a fluorescent image of the donor organ or the vessel attached to a donor organ, and observing the image to determine if a fluorescent signal is continuous through the vessel. A continuous fluorescent signal in the donor organ or vessel indicates the respective donor organ or vessel is patent.

20 Claims, 2 Drawing Sheets

(56) References Cited

U.S. PATENT DOCUMENTS

| | | | |
|---|---|---|---|
| 6,631,286 | B2 | 10/2003 | Pfeiffer |
| 6,804,549 | B2 | 10/2004 | Hayashi |
| 6,821,946 | B2 | 11/2004 | Goldspink et al. |
| 6,840,933 | B1 | 1/2005 | Pang et al. |
| 6,853,857 | B2 | 2/2005 | Pfeiffer et al. |
| 6,882,366 | B1 | 4/2005 | Kijima et al. |
| 6,899,675 | B2 | 5/2005 | Cline et al. |
| 6,915,154 | B1 | 7/2005 | Docherty et al. |
| 6,944,493 | B2 | 9/2005 | Alam et al. |
| 7,881,777 | B2 | 2/2011 | Docherty et al. |
| 8,647,605 | B2 * | 2/2014 | Mangat .............. A61K 49/0034 424/9.6 |
| 8,892,190 | B2 | 11/2014 | Docherty et al. |
| 2003/0156252 | A1 | 8/2003 | Morris et al. |
| 2003/0187349 | A1 | 10/2003 | Kaneko et al. |
| 2003/0232016 | A1 | 12/2003 | Heinrich |
| 2004/0109231 | A1 | 6/2004 | Haisch et al. |
| 2004/0156782 | A1 | 8/2004 | Alam et al. |
| 2005/0069525 | A1 | 3/2005 | Mikael |
| 2005/0107380 | A1 | 5/2005 | Nimmo et al. |
| 2005/0182321 | A1 | 8/2005 | Frangioni |
| 2005/0182434 | A1 | 8/2005 | Docherty et al. |
| 2005/0197583 | A1 | 9/2005 | Chance |
| 2006/0108509 | A1 | 5/2006 | Frangioni et al. |
| 2006/0239921 | A1 | 10/2006 | Mangat et al. |
| 2006/0241499 | A1 | 10/2006 | Irion et al. |
| 2007/0203413 | A1 | 8/2007 | Frangioni |
| 2015/0112192 | A1 | 4/2015 | Docherty et al. |
| 2015/0112193 | A1 | 4/2015 | Docherty et al. |

FOREIGN PATENT DOCUMENTS

| | | | |
|---|---|---|---|
| CN | 1049781 | A | 3/1991 |
| CN | 1200174 | A | 11/1998 |
| EP | 0 091 805 | A2 | 10/1983 |
| EP | 0 826 335 | A1 | 3/1998 |
| JP | S-59-069721 | A | 4/1984 |
| JP | S-59-070903 | A | 4/1984 |
| JP | 02-200237 | A | 8/1990 |
| JP | 04-297236 | A | 10/1992 |
| JP | 06-335451 | A | 12/1994 |
| JP | 07-065154 | A | 3/1995 |
| JP | 07-079955 | A | 3/1995 |
| JP | 07-222712 | A | 8/1995 |
| JP | 08-024227 | A | 1/1996 |
| JP | H-5-264232 | A | 10/1996 |
| JP | H-09-120033 | A | 5/1997 |
| JP | A-9-305845 | A | 12/1997 |
| JP | H-09-308609 | A | 12/1997 |
| JP | 10-085222 | A | 4/1998 |
| JP | 10-506550 | A | 6/1998 |
| JP | H-10-201707 | A | 8/1998 |
| JP | H-11-137517 | A | 5/1999 |
| JP | H-11-509748 | A | 8/1999 |
| JP | 3-115958 | A | 11/2005 |
| JP | 3-896176 | B2 | 3/2007 |
| JP | A 9-309845 | | 12/2007 |
| WO | WO 9325141 | A1 | 12/1993 |
| WO | WO-94/12092 | A1 | 6/1994 |
| WO | WO-96/09792 | A1 | 4/1996 |
| WO | WO-96/18415 | A1 | 6/1996 |
| WO | WO-96/23524 | A1 | 8/1996 |
| WO | WO-96/39925 | A1 | 12/1996 |
| WO | WO-97/08538 | A1 | 3/1997 |
| WO | WO-98/30144 | A1 | 7/1998 |
| WO | WO-98/46122 | A1 | 10/1998 |
| WO | WO-99/00053 | A1 | 1/1999 |
| WO | WO-99/47940 | A1 | 9/1999 |
| WO | WO-01/17561 | A1 | 3/2001 |
| WO | WO-01/22870 | A1 | 4/2001 |
| WO | WO-2006/121631 | A2 | 11/2006 |
| WO | WO-2006/121631 | A3 | 11/2006 |
| WO | WO-2008/070269 | A2 | 6/2008 |
| WO | WO-2008/070269 | A3 | 6/2008 |

OTHER PUBLICATIONS

Paques et al., "Axon-Tracing Properties of Indocyanine Green," Arch Ophthalmol, 121:367-370, (2003).

Parungo et al., "Intraoperative identification of esophageal sentinel lymph nodes with near-infrared fluorescence imaging," The Journal of Thoracic and Cardiovascular Surgery, 129(4):844-850, (2005).

Raabe et al., "Near-Infrared Indocyanine Green Video Angiography: A New Method for Intraoperative Assessment of Vascular Flow," Neurosurgery, 52(1):132-139, (2003).

Ross et al., "The ability of lymphoscintigraphy to direct sentinel node biopsy in the clinically N0 neck for patients with head and neck squamous cell carcinoma," The British Journal of Radiology, 75:950-958, (2002).

Rubben et al., "Infrared Videoangiofluorography of the Skin with Indocyanine Green-Rat Random Cutaneous Flap Model and Results in Man," Microvascular Research, 47:240-251, (1994).

Schneider et al., "Fluorescence of Testicle, An Indication of Viability of Spermatic Cord After Torsion" Urology, V(1):133-136, (1975).

Sekijima et al., "An Intraoperative Fluorescent Imaging System in Organ Transplantation," Transplantation Proceedings, 36:2188-2190, (2004).

Sherif et al., "Lymphatic Mapping and Detection of Sentinel Nodes in Patients with Bladder Cancer," The Journal of Urology, 166:812-815, (2001).

Soltesz et al., "Intraoperative Sentinel Lymph Node Mapping of the Lung Using Near-Infrared Fluorescent Quantum Dots," Ann Thorac Surg 79:269-277, (2005).

Still et al., "Diagnosis of burn depth using laser-induced indocyanine green fluorescence: a preliminary clinical trial," Burns, 27:364-371, (2001).

Dan et al., "1% Lymphazurin vs 10% Fluorescein for Sentinel Node Mapping in Colorectal Tumors," Arch Surg, 139:1180-1184, (2004).

DeGrand et al., "An Operational Near-Infrared Fluorescence Imaging System Prototype for Large Animal Surgery," Technology in Cancer Research & Treatment, 2(6):1-10, (2003).

Demos, "Near-infrared autofluorescence imaging for detection of cancer," Journal of Biomedical Optics, 9(3):587-592, (2004).

Dietz et al., "Indocyanine Green, Evidence of Neurotoxicity in Spinal Root Axons," Anesthesiology, 98(2):516-520, (2003).

Frangioni "In vivo near-infrared fluorescence imaging," Current Opinion in Chemical Biology, 7:626-634, (2003).

Haglund et al., "Enhanced Optical Imaging of Rat Gliomas and Tumor Margins," Congress of Neurological Surgeons, 35(5):930-941, (1994).

Herts, "Imaging for renal tumors," Current Opin Urol, 13:181-186, (2003).

Humblet et al., "High-affinity Near-infrared Fluorescent Small-molecule Contrast Agents for In Vivo Imaging of Prostate-specific Membrane Antigen," Molecular Imaging, 4(4):448-462, (2005).

Kamolz et al., "Indocyanine green video angiographies help to identify burns requiring operation," Burns, 29:785-791, (2003).

Kim et al., "Near-infrared fluorescent type II quantum dots for sentinel lymph node mapping," Nature Biotechnology, 22(1):93-97, (2004).

Liedberg et al., "Intraoperative Sentinel Node Detection Improves Nodal Staging in Invasive Bladder Cancer," The Journal of Urology, 175:84-89, (2006).

Liedberg et al., Sentinel-Node-Diagnostik beim invasiven (Bladder Cancer and the Sentinel Node Concept), Aktuel Urol, 34:115-118, (2003).

Malmstrom et al., "Early Metastatic Progression of Bladder Carcinoma: Molecular Profile of Primary Tumor and Sentinel Lymph Node," The Journal of Urology, 168:2240-2244, (2002).

Marangos et al., "In vivo visualization of the cochlear nerve and nuclei with fluorescent axonal tracers," Hearing Research, 162:48-52, (2001).

Motomura et al. "Sentinel Node Biopsy Guided by Indocyanine Green Dye in Breast Cancer Patients," Jpn J Olin Oncol, 29(12):604-607, (1999).

Nakayama et al., "Functional Near-Infrared Fluorescence Imaging for Cardiac Surgery and Targeted Gene Therapy," Molecular Imaging, 1(1):365-377, (2002).

(56) References Cited

OTHER PUBLICATIONS

Nimura et al., "Infrared ray electronic endoscopy combined with indocyanine green injection for detection of sentinel nodes of patients with gastric cancer," British Journal of Surgery, 91:575-579, (2004).
Argus-50/CA, Inter cellular CA2+ (calcium ion) Image Analysis system, Observation and 2-dimensional analysis of Ca2+ concentration distribution. Fura-2 and Indo-1 compatible. Ca2+ concentrations are calculated from the fluorescence ratio, Feb. 1992, pp. 1-10.
Balacumarswami, L. et al. (Aug. 2004). Does off-pump total arterial grafting increase the ndicent of intraoperative failure? Cardiopulmonary Support and Physiology, *The Journal of Thoracic and Cardiovascular Surgery*128(2):238-244.
Barton, J.K. et al. (1999). "Simultaneous irradiation and imaging of blood vessels during pulsed laser delivery." *Lasers in Surgery and Medicine*24(3):236-243.
Benson, R.C. et al. (1978). "Fluorescence Properties of Indocyanine Green as Related to Angiography," *Phys. Med. Biol.* 23(1):159-163.
Boer, F. et al., "Effect of ventilation on first-pass pulmonary retention of alfentaril and sufentanil in patients undergoing coronary artery surgery,"British Journal Anesthesia, 73:458-463, (1994).
Boldt, J. et al. (1991). "Does the technique of cardiopulmonary bypass affect lung water content?" *Eur. J. Cardio-Thorac. Surg.* 5:22-26.
Boldt, B.J. et al. (Feb. 1990). "Lung management during cardiopulmonary bypass: influence on extravascular lung water," *J. Cardiothorac Anesth.* 4(1):73-79.
C2741, Compact High Performance video camera for industrial applications with Built-in contrast enhancement circuit, Jun. 1998.
Decision in Opposition Proceeding Revoking (Jun. 10, 2010). European Patent No. 1 143 852, thirty pages.
Desai, N.D. et al. (2005). "Improving the Quality of Coronary Bypass Surgery with Untraoperative Angiography," *JACC*46(8):1521-1525.
Digital CCD Microscopy, Chapter 14, pp. 259-282, date unknown.
Emery, R.W. et al. (1996). "Revascularization Using Angioplasty and Minimally Invasive Techniques Documented by Thermal Imaging," *The Society of Thoracic Surgeon*62:591-593.
Eren, S. et al. (Dec. 1995). "Assessment of Microcirculation of an Axial Skin Flap Using Indocyanine Green Fluorescence Angiography," *Plast. Reconstr. Surg.* 96(7):1636-1649.
Extended European Search Report for EP 10 18 621.8, mailed Dec. 16, 2010.
Final Office Action mailed on Sep. 23, 2004, for U.S. Appl. No. 09/744,034, filed Apr. 27, 2001, seven pages.
Final Office Action mailed on Apr. 10, 2008, for U.S. Appl. No. 11/106,154, filed Apr. 14, 2005, six pages.
Final Office Action mailed on Feb. 18, 2010, for U.S. Appl. No. 11/106,154, filed Apr. 14, 2005, six pages.
Final Office Action mailed on Sep. 13, 2011, for U.S. Appl. No. 11/106,154, filed Apr. 14, 2005, five pages.
Final Office Action mailed on Nov. 6, 2013, for U.S. Appl. No. 13/419,368, filed Mar. 13, 2012, five pages.
Final Office Action mailed on Apr. 2, 2013, for U.S. Appl. No. 13/419,368, filed Mar. 13, 2012, five pages.
Final Office Action mailed on Jul. 9, 2015, for U.S. Appl. No. 14/543,356, filed Nov. 17, 2014, eight pages.
Final Office Action mailed on Feb. 13, 2015, for U.S. Appl. No. 14/543,429, filed Nov. 17, 2014, six pages.
Final Office Action mailed on Jun. 1, 2015, for U.S. Appl. No. 14/543,429, filed Nov. 17, 2014, nine pages.
Final Office Action mailed on Aug. 10, 2012, for U.S. Appl. No. 11/912,877, filed Aug. 13, 2008, eleven pages.
Flower, R.W. (1992). "Choroidal Angiography Today and Tomorrow," Retina, 12(3):189-190.
Flower, R.W. (Sep. 1994). "Does Preinjection Binding of Indocyanine Green to Serum Actually Improve Angiograms," *Arch Ophthalmol.* 112:1137-1139.
Flower, R.W. (1977). "Quantification of Indicator Dye Concentration in Ocular Blood Vessesls," *Exp. Eye Res.* 25:103-111.
Flower, R. et al. (1999). "Effects of free and liposome-encapsulated hemoglobin on choroidal vascular plexus blood flow, using the rabbit eye as a model system," *European Journal of Ophthalmology*9(2):103-114.
Goldstein, J.A. et al. (1998). "Intraoperative Angiography to Assess Graft Patency After Minimally Invasive Coronary Bypass," *Anna Thorac Surg.* 66:1978-1982.
Green, H.A. et al. (Jan. 1992). "Burn Depth Estimation Using Indocyanine Green Fluorescence," *Arch Dermatol.* 128:43-49.
Hamamatsu Brochure, Specifications for ARGUS-20 with C2400-75i (May 1997).
Hayashi, J. et al. (1993). "Transadventitial localization of atheromatous plaques by fluorescence emission spectrum analysis of mono-L aspartyl-chlorin e6," Cardiovascular Research, 27:1943-1947.
International Search Report mailed on Oct. 18, 2000, for PCT Application No. PCT/US2000/22088, filed on Aug. 11, 2000, one page.
International Searching Authority, "International Preliminary Examination Report from PCT/US00/22088 (N001/7000WO)," Aug. 11, 2000, Patent Cooperation Treaty, three pages.
Jagoe, J.R. et al. "Quantification of retinal damage during cardiopulmonary bypass," Third International Conference on Image Processing and its Applications (Conf. Publ. No. 307), IEE, 1989, pp. 319-323.
Keon et al. (1979). "Coronary endarterectomy: An adjunct to coronary artery bypass grafting," *Surgery*86(6):859-867.
Kitai et al. (2005). "Fluorescence Navigation with Indocyanine Green for Detecting Sentinel Lymph Nodes in Breast Cancer," *Breast Cancer*12(3):211-215.
Kokaji et al., "Intraoperative Quality Assessment by Using Fluorescent Imaging in Off-pump Coronary Artery Bypass Grafting," The Department of Cardiovascular Surgery, University of Keio, Tokyo, Japan. (Abstract only).
Kyo et al., "Use of Ultrasound Cardiology during Coronary Artery Bypass Surgery," Heart and Blood Vessel Imaging II.
Laub, G.W. et al. (1989). "Experimental Use of Fluorescein for Visualization of Coronary Arteries," *Vascular Surgery*12(6):454-457.
Lee, E.T. et al. (Mar. 1997.). "A new Method for Assessment of Changes in Retinal Blood Flow," *Med. Engineering & Physics*19(2): 125-130.
Lund, F. et al. (Nov. 1997). "Video Fluorescein Imaging of the Skin: Description of an Overviewing Technique for Functional Evaluation of Regional Cutaneous Blood Evaluation of Regional Cutaneous Perfusion in Occlusive Arterial Disease of the Limbs,"*Clinical Physiology*17(6):619-633.
May, S.A. (May/Jun. 1995). "Photonic Approaches to Burn Diagnostics," Biophotonics International, pp. 44-50.
Microscope Video Camera, For Fluorescent Observation, Easy Fluorescent Image Analysis a CCD Camera.
Mohr, F.W. et al. (1997). "Thermal Coronary Angiography: A Method for Assessing Graft Patency and Coronary Anatomy in Coronary Bypass Surgery," The Society of Thoracic Surgeons, No. 63, Elsevier Science Inc., pp. 1506-1507.
Murphy, D.B. (2001). "Digital CCD Microscopy,"Chapter 14 in *Fundamentals of Light Microscopy and Elecronic Imaging,* John Wiley and Sons, pp i-xi and 259-281.
Nakamura, T. et al. (1964). "Use of Novel Dyes, Coomassie Blue and Indocyanine Green in Dye Dilutin Method,"Tohoka University, Nakamura Internal Department, The Tuberculosis Prevention Society, Tuberculosis Research Laboratory, 17(2):1361-1366.
Non-Final Office Action mailed on Mar. 10, 2004, for U.S. Appl. No. 09/744,034, filed Apr. 27, 2001, seven pages.
Non-Final Office Action mailed on Mar. 6, 2007, for U.S. Appl. No. 11/106,154, filed Apr. 14, 2005, eight pages.
Non-Final Office Action mailed on Jan. 9, 2009, for U.S. Appl. No. 11/106,154, filed Apr. 14, 2005, six pages.
Non-Final Office Action mailed on Sep. 15, 2010, for U.S. Appl. No. 11/106,154, filed Apr. 14, 2005, six pages.
Non-Final Office Action mailed on Dec. 30, 2010, for U.S. Appl. No. 11/946,672, filed Apr. 14, 2007, six pages.
Non-Final Office Action mailed on Apr. 28, 2010, for U.S. Appl. No. 11/946,672, filed Nov. 28, 2007, nine pages.

(56) References Cited

OTHER PUBLICATIONS

Non-Final Office Action mailed on Mar. 13, 2015, for U.S. Appl. No. 14/543,356, filed Nov. 17, 2014, eight pages.
Non-Final Office Action mailed on Nov. 27, 2015, for U.S. Appl. No. 14/543,429, filed Nov. 17, 2014, six pages.
Non-Final Office Action mailed on Jan. 27, 2012, for U.S. Appl. No. 11/912,877, filed Aug. 13, 2008, eleven pages.
Notice of Allowance mailed on Oct. 4, 2013, for U.S. Appl. No. 11/912,877, filed Aug. 13, 2008, nine pages.
Notice of Allowance mailed on Mar. 7, 2005, for U.S. Appl. No. 09/744,034, filed Apr. 27, 2001, five pages.
Notice of Allowance mailed on Nov. 30, 2010, for U.S. Appl. No. 11/946,672, filed Nov. 28, 2007, six pages.
Notice of Allowance mailed on Apr. 17, 2014, for U.S. Appl. No. 13/419,368, filed Mar. 13, 2012, five pages.
Notice of Allowance mailed on Oct. 6, 2014, for U.S. Appl. No. 13/419,368, filed Mar. 13, 2012, five pages.
Ogata et al. (2007). "Novel Lymphography Using Indocyanine Green Dye for Near-Infrared Fluorescence Labeling," *Annals of Plastic Surgery*58(6):652-656.
Ooyama, Masa, (Oct. 12, 1994). "The 8$^{th}$ Congress of International YAG Laser Symposium," The 15$^{th}$ Annual Meeting of Japan Society for Laser Medicine, Sun Royal Hotel.
Opposition of European Patent No. EP1143852 lodged by Hamamatsu Photonics, Inc.
Ott, "Hepatic Elimination of Indocyanine Green with Special Reference to Distribution Kinetics and the Influence of Plasma Protein Binding," Thesis.
Phillips, R.P. et al. (1991). "Quantification of Diabetic Maculopathy by Digital Imaging of the Fundus," *Eye*5(1):130-137.
Report on Observation by C2400-75i and ARGUS20 Under Low illumination conditions, Jan. 17, 2008.
Request for Invalidation of Japanese Patent JP3881550 filed by Hamamatsu Photonics, Inc. (with English Translation).
Reuthebuch, O. et al. (2004). "Novadaq SPY: Intraoperative Quality Assessment in Off Pump Coronary Artery Bypass Grafting," *Chest*125(2): 418-424.
Reuthebuch, O.T. et al. (2003). "Graft occlusion after deployment of the symmetry bypass system," *Ann. Thorac. Surg.* 75:1626-1629.
Roberts, W.W. et al. (1997). "Laparoscopic Infrared Imaging," *Surg. Endoscopy*11:1221-1223.
Rubens, F.D. et al. (2002). "A new and Simplified method for coronary and graft imaging during CABG," *The Heart Surgery Forum*5(2):141-144.
Sakatani, K. et al. (1997). "Noninvasive Optical Imaging of the Subarchnoid Space and Cerebrospinal Fluid Pathways Based on Near Infrared Fluorescence," *J. Neurosurg.* 87:738-745.
Salmon et al. (1994). "High Resolution Multimode Digital Imaging System for Mitosis Studies in Vivo and Vitro," *Biol. Bull.* 187:231-232.
Sato, et al., (1991). "Development of a Deep Organ Microcirculation Visualization Techniques Using an Infrared Biomicroscpoe System," Research Report from Suzuken Memorial Foundation, vol. 9, pp. 63-73 and 228. (with English Translation).
Siemers, B.M. et al. (2001). The acoustic advantage of hunting at low heights above water: behavioual experiments on the European 'trawling' bats *Myotis capaccinii, M dasycneme* and *M. daubentonii*, J. Eperimental Biol. 204:3843-3854.
Skalidis et al. (2004). "Regional Coronary Flow and Contractile Reserve in Patients with Idiopathic Dilated Cardiomyopathy," *Journal of the American College of Cardiology*44(10):2027-2032.
Still, J. et al. (1999). Evaluation of the Circulation of Reconstructive Flaps Using Laser-Induced Fluorescence of Indocyanine Green, *Annals of Plastic Surgery*42(42):266-274.
Suma, H. et al. (2000). "Coronary Artery Bypass Grafting Without Cardiopulmonary Bypass in 200 Patients," *Cardiol.* 36(2):85-90ac (English Abstract).
Supplemental European Search Report for EP Application No. 00 955 472, mailed on Jul. 6, 2004, five pages.
Taggart et al. (2003). "Preliminary experience with a novel intraoperative fluorescence imaging technique to evaluate the patency of bypass grafts in total arterial revascularization," Department of Cardiothoracic Surgery, John Radcliffe Hospital, Oxford, United Kingdom, pp. 870-875.
Taichman et al. (1987). "The Use of Cardio-Green for Intraoperative Visualization of the Coronary Circulation: Evaluation of Myocardial Toxicity," *Tex Heart Inst. J.*, 14(2):133-138.
Takahashi et al. (2004). "SPY: an innovative intra-operative imaging system to evaluate graft patency during off-pump coronary artery bypass grafting," *Interactive CardioVascular and Thoracic Surgery* 3:479-483.
Takayama, T., "Intraoperative Coronary Angiography Using Fluorescein," *The Annals of Thoracic Surgery*51(1):140-143.
Takayama et al. (1992). "Intraoperative Coronary Angiography Using Fluorescein Basic Studies and Clinical Application," *Vascular Surgery*26(3):193-199.
Taylor, K.M. (Apr. 1998). "Brain Damage During Cardiopulmonary Bypass," *Annals of Thoracic Surgery*65(4):S20-S26.
Torok, B. et al. "{Simultaneous digital indocyanine green and fluorescein angiography}" Klinische Monatsblatter Fur Augenheilkunde, May 1996, vol. 208, No. 5, May 1996, pp. 333-336.
Tsutsumi et al. "Moisture Detection of road surface using infrared camera," Reports of the Hokkaido Industrial Research Institute (No. 297), Issued on Nov. 30, 1998.
Unno et al. (2007). "Indocyanine Green Fluorescence Angiography for intraoperative assessment of Blood flow: A Feasibility Study," *Eur. J. Vasc. Endovasc. Surg.*, pp. 1-3.
Van Son et al., "Thermal Coronary Angiography for Intraoperative Testing of Coronary Patency in Congenital Heart Defects," *The Society of Thoracic Surgeons*64:1499-1500.
Wachi et al. (1995). "Characteristics of cerebrospinal fluid circulation in infants as detected with MR velocity imaging," *Child's Nerv. System*11:227-230.
What is Perfusion? A Summary of Different Typed of Perfusion. (Sep. 1, 2004). Located at, http://www.perfusion.com/cgi-bin/absolutenm/templates/articledisplay.asp?articleid=1548#.Vo8Hv02FPGj, last visited on Jan. 7, 2016, two pages.
Wise et al. (2005). "Simultaneous Measurement of Blood and Myocardial velocity in the Rat Heart by Phase Contrast MRI Using Sparse q-Space sampling" Journal of Magnetic Resonance Imaging 22:614-627.
Woitzik et al. (2005). "Intra operative control of extracranial-intracranial bypass patency by near-infrared indocyanine green videoangiography," *J. Neurosurg.* 102:692-698.
Wollert, H.G. et al. (Dec. 1989). "Intraoperative Visualization of Coronary Artery Fistula Using Medical Dye," *The Thoracic and Cardiovascular Surgeon*46(6):382-383.
Yada, et al. (May 1993). "In vivo observation of subendocardial microvessels of the beating porcine heart using a needle-probe videomicroscope with a CCD camera," *Journal of the American Heart Association* 72(5):939-946.
Yoneya et al. (1998). "Binding Properties of Indocyanine Green in Human Blood," *IOVS*39(7):1286-1290.
Yoneya et al. (1993). "Improved Visualization of the Choroidal circulation with Indocyanine Green angiography," *Arch Opthalmol,* 11:1165-1166.
Young et al. "Depth of Focus in Microscopy," SCIA '93, Proc. Of the 8$^{th}$ Scandinavian Conference on Image Analysis, Tromso, Norway, 1993, pp. 493-498.
U.S. Appl. No. 14/379,290, filed Sep. 28, 2015, by Brzozowski et al. (Copy not attached).

\* cited by examiner

REAL TIME IMAGING DURING SOLID ORGAN TRANSPLANT

CROSS-REFERENCES TO RELATED APPLICATIONS

This application is a divisional of U.S. application Ser. No. 11/912,877, filed Aug. 13, 2008, which was filed under 35 U.S.C. 371 as a U.S. national phase application of PCT Application No. PCT/US2006/016089, filed Apr. 26, 2006, which is a continuation of U.S. application Ser. No. 11/114,501, filed Apr. 26, 2005, the disclosures of all of which are incorporated herein by reference in their entirety as if fully set forth herein.

FIELD OF THE INVENTION

The invention relates generally to the field of medical imaging. Certain embodiments of the invention provide methods for imaging of vasculature in a subject. Certain other embodiments provide systems which are useful for imaging vasculature in a subject.

BACKGROUND OF THE INVENTION

Imaging of biological tissues and organs assists doctors in both diagnosis and treatment. A variety of medical techniques which are suitable for imaging biological tissues and organs are known. These include traditional x-rays, ultra-sound, as well as magnetic resonance imaging (MRI), and computerized tomography (CT). A variety of dyes used in medical imaging have also been described including radio opaque dyes, fluorescent dyes, as well as, colormetric dyes (see e.g., U.S. Pat. Nos. 5,699,798; 5,279,298; 6,351,663; and 6,915,154 and U.S. patent application Ser. Nos. 10/619,548 and 10/365,028). Imaging techniques and systems using fluorescent dyes have been described for the heart and eye (see, U.S. Pat. No. 5,279,298; U.S. patent application Ser. No. 10/619,548, which is incorporated by reference in its entirety). Some dyes can serve both an imaging function, as well as a therapeutic function (see, e.g. U.S. Pat. No. 6,840,933).

Organ transplant is one area in which imaging methods and systems would prove useful. The demand for organ transplant continues to grow. The combined number of solid organ transplants in the US alone, is approximately 18,000 per year. Specifically the combined numbers for years 1997 and 1998 were: 1,692 lung transplants, 4,409 heart, 7,502 liver, 326 pancreas, 1,803 pancreas and kidney, and 20,956 kidney transplants (see, e.g., *The U.S. Organ Procurement and Transplantation Network and the Scientific Registry of Transplant Recipients Annual Report,* 2004).

Transplant procedures involve anastomosis. These anastomoses may be between, for example, two vessels, vessels and duct(s), two ducts, or vessels and ureter(s), two parts of a ureter, or the ureter and bladder. As such, solid organ transplant procedures would benefit from the pre-operative assessment of the patency of vessels, ducts, and ureters of the donor organs, and intra-operative and post-operative verification of anastomoses and the patency of blood vessels, ducts, and ureters of the transplanted organs, as well as other recipient blood vessels, ducts, and ureters. It would be particularly useful to provide real time, i.e. intra-operative visual confirmation regarding the verification of anastomoses and patency of vessels, e.g. vasculature. Traditional intra-operative imaging techniques, are frequently ineffective, expensive and inconvenient. The need therefore exists for methods and systems for imaging vessels associated with solid organ transplants which are safe, effective, convenient and cost effective.

SUMMARY OF THE INVENTION

In certain embodiments the invention provides a method of intra-operatively determining the patency of at least one vessel which is surgically joined to a transplanted organ in a recipient subject comprising: a) administering a fluorescent dye to the recipient subject; b) applying a sufficient amount of energy to the vessel such that the fluorescent dye fluoresces; c) obtaining a fluorescent image of the vessel surgically joined to a transplanted organ; and d) observing the image to determine if a fluorescent signal is continuous through the vessel, wherein a continuous fluorescent signal in the vessel indicates the vessel is patent.

In some embodiments, the invention provides a method of determining the patency of at least one vessel which is attached to a donor organ in a donor. The method includes the steps of (a) administering a fluorescent dye to the donor subject; (b) applying a sufficient amount of energy to the vessel such that the fluorescent dye fluoresces; (c) obtaining a fluorescent image of the vessel attached to a donor organ; and (d) observing the image to determine if a fluorescent signal is continuous through the vessel, wherein a continuous fluorescent signal in the vessel indicates the vessel is patent.

In some embodiments, the invention provides a method of determining the patency of a donor organ. The method includes the steps of (a) administering a fluorescent dye to the vessel attached to the donor organ; (b) applying a sufficient amount of energy to the vessel such that the fluorescent dye fluoresces; (c) obtaining a fluorescent image of the donor organ; and (d) observing the image to determine if a fluorescent signal is continuous through the donor organ, wherein a continuous fluorescent signal in the donor organ indicates the donor organ is patent. Either the entire or less than the entire donor organ may be imaged according to the methods of the invention.

BRIEF DESCRIPTION OF THE DRAWINGS

The above and further advantages of the invention may be better understood by referring to the following description in conjunction with the accompanying drawings in which.

DETAILED DESCRIPTION

Figure 1:
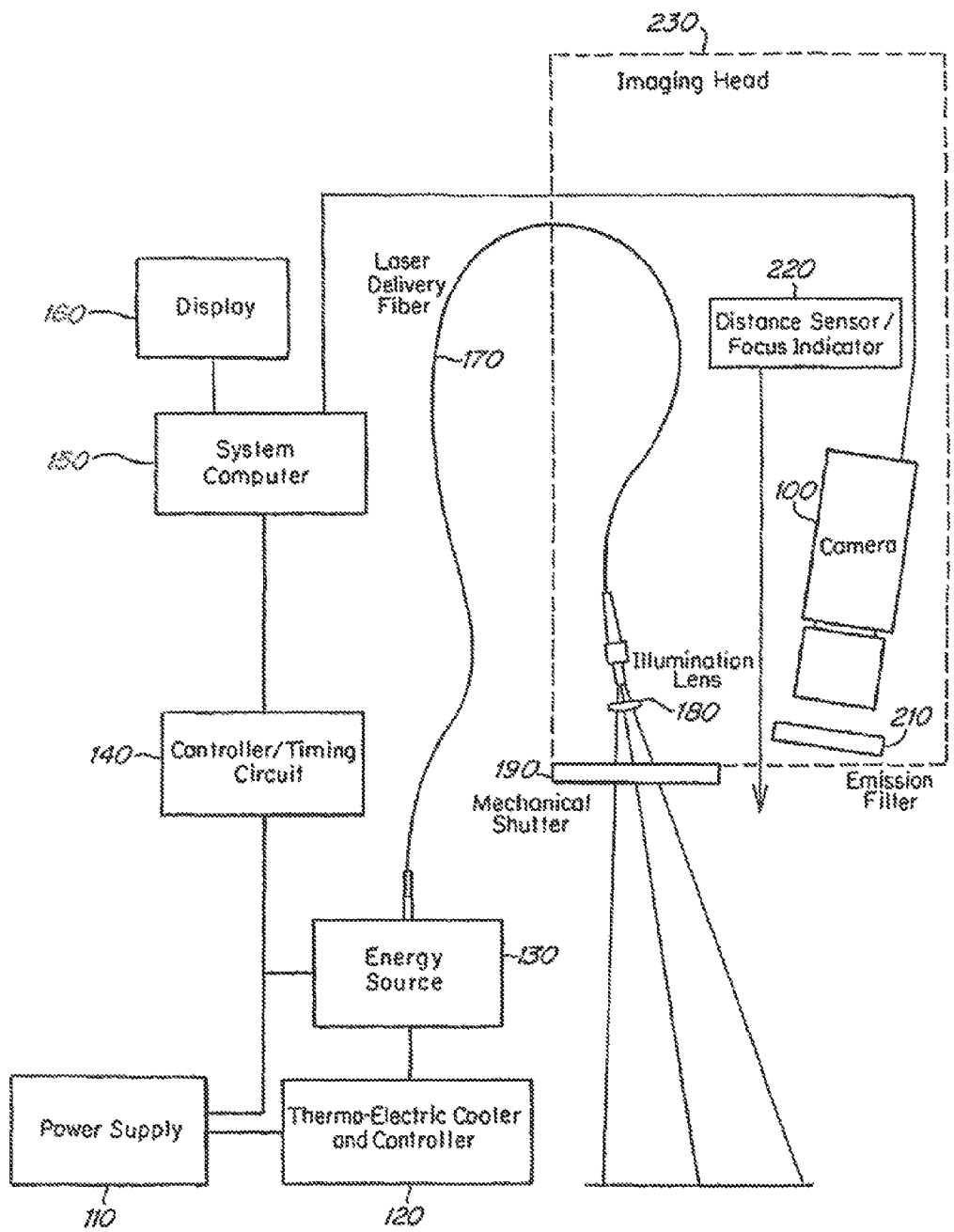
FIG. 1 shows an example of an electrical configuration of a system of the invention.

Hereinafter, aspects in accordance with various embodiments of the invention will be described. As used herein, any term in the singular may be interpreted to be in the plural, and alternatively, any term in the plural may be interpreted to be in the singular.

Organ transplants of various types are performed routinely. Solid organ transplants of all types require the joining of vessels, e.g., blood vessels in order to attach the donor organ. Some organ transplants, such as a pancreas transplant also require the joining of a duct to a lumen, e.g. the pancreatic duct to the digestive tract. Occlusion, due to, thrombosis, plaque, or free floating endothelial material, for example, is a risk associated with transplant surgery. The invention described herein, in certain embodiments, provides a method and a system which a surgeon can use intra-operatively to determine if an anastomosis created during transplant surgery is patent. The invention also provides a method and system to determine, pre-surgery, if a donor organ, or a vessel attached to a donor organ, is patent.

"Approximately", "substantially" and "about" each mean within 10%, preferably within 6%, more preferably within 4% even more preferably within 2%, and most preferably within 0.5%.

Subject as used herein, refers to any animal. The animal may be a mammal. Examples of suitable mammals include, but are not limited to, humans, non-human primates, dogs, cats, sheep, cows, pigs, horses, mice, rats, rabbits, and guinea pigs.

Recipient subject, as used herein, refers to a subject that is receiving a solid organ transplant.

Computer, as used herein, refers to a conventional computer as understood by the skilled artisan. For example, a computer generally includes a central processing unit that may be implemented with a conventional microprocessor, a random access memory (RAM) for temporary storage of information, and a read only memory (ROM) for permanent storage of information. A memory controller is provided for controlling RAM. A bus interconnects the components of the computer system. A bus controller is provided for controlling the bus. An interrupt controller is used for receiving and processing various interrupt signals from the system components. Mass storage may be provided by diskette, CD ROM or hard drive. Data and software may be exchanged with computer system via removable media such as the diskette or CD ROM. A CD ROM drive is connected to the bus by the controller. The hard disk is part of a fixed disk drive that is connected to the bus by a controller. User input to the computer may be provided by a number of devices. For example, a keyboard and mouse may be connected to the bus by a controller. An audio transducer that might act as both a microphone and a speaker may be connected to the bus by an audio controller. It will be obvious to those reasonably skilled in the art that other input devices, such as a pen and/or tablet may be connected to the bus and an appropriate controller and software, as required. A visual display can be generated by a video controller that controls a video display. Preferably, the computer further includes a network interface that allows the system to be interconnected to a local area network (LAN) or a wide area network (WAN). Operation of the computer is generally controlled and coordinated by operating system software, such as the Solaris operating system, commercially available from Sun Microsystems, the UNIX® operating system, commercially available from The Open Group, Cambridge, Mass., the OS/2® operating system, commercially available from International Business Machines Corporation, Boca Raton, Fla., or the Windows NT operating system, commercially available from Microsoft Corp., Redmond, Wash. The operating system controls allocation of system resources and performs tasks such as processing scheduling, memory management, networking, and I/O services, among things. In particular, an operating system resident in system memory and running on the CPU coordinates the operate of the other elements of computer.

Donor subject, as used herein, refers to a subject that is donating a solid organ for transplant. The donor subject may be alive or dead (i.e., a cadaver).

Duct, as used herein, refers to a vessel having a lumen in which a liquid is carried or transported. In some living organisms ducts are found for example in liver and in glands, such as sweat glands, or the pancreas. The pancreas secretes digestive enzymes via a duct, however, it also secretes insulin from the Islets of Langerhans directly into the blood without any duct.

Arterial graft, as used herein, refers to a natural or synthetic vessel, which delivers blood to a transplanted solid organ. It can be derived from the donor subject, the recipient subject, or a different subject. It can include a vessel made from a synthetic material, or a naturally derived material (i.e. from a living organism) or a combination of a natural and synthetic material.

Venous graft, as used herein, refers to a natural or synthetic vessel, which drains blood from a transplanted solid organ. It can be derived from the donor subject, the recipient subject, or a different subject. It can include a vessel made from a synthetic material, or a naturally derived material (i.e. from a living organism) or a combination of a natural and synthetic material.

Vessel as used herein includes any tube having a lumen capable of transporting a fluid within a subject e.g., veins, arteries and ducts.

Methods of the Invention

In certain embodiments the invention provides a method of intra-operatively determining the patency of at least one vessel, or at least one anastomosis between two vessels, or at least one anastomosis between a vessel and an intervening duct or vessel of an organ, or at least one anastomosis between a vessel and an organ, where the vessel is surgically joined to a transplanted organ in a recipient subject. The method comprises administering a fluorescent dye to the subject and exposing at least one of the transplanted organ, the vessel, and the anastomosis, to a form of radiant energy, such that the fluorescent dye fluoresces and obtaining an image of at least one of the vessel, the anastomosis, and the transplanted solid organ. The image may be obtained intra-operatively. Thus, in some embodiments, the vessel may be a surgically exposed vessel which communicates with the transplanted organ.

The invention also contemplates, in some embodiments, obtaining a plurality of images. The plurality of images may be compared to each other to determine the effectiveness of a therapy, e.g. an administered pharmaceutical compound, a surgical procedure.

In certain embodiments the invention provides a method for determining the patency of a vessel attached to a donor organ, or determining the patency of a donor organ itself. The method comprises a) administering a fluorescent dye to the donor subject or donor organ; b) applying a sufficient amount of energy to the donor organ and attached vessel such that the fluorescent dye fluoresces; c) obtaining a fluorescent image of the donor organ, or a fluorescent image of the vessel attached to the donor organ; and d) observing the image to determine if a fluorescent signal is continuous through the donor organ or the vessel attached to the donor organ, wherein a continuous fluorescent signal in the vessel, or the organ indicates the vessel is patent.

In certain embodiments the invention provides a method of determining the patency of a vessel comprising a lumen. In some embodiments patency may be determined by visually inspecting an image of the vessel. As an example, but not as a limitation, a continuous signal from a dye that is uniform in thickness may indicate patency. As another non-limiting example an image displaying jagged edges, or a change in thickness may indicate stenosis. Similarly a discontinuous signal may indicate occlusion.

Solid Organs

The method of the invention may be used in any organ transplant surgery provided at least one vessel from the recipient communicates either directly, or indirectly, e.g., via an intervening vessel, with the transplanted organ, or a vessel attached to the transplanted organ. The organ may be a natural organ obtained from a donor subject or man-made synthetic organ, or a combination of the two, i.e., part naturally derived and part synthetic. Transplants involving more than one organ are also contemplated by the invention. The vessel may be synthetic, i.e., man-made or natural, i.e. derived from a biological source, including an allograft, an autograft and a xenograft, or a combination of a biological and synthetic source.

As an example, but not as a limitation, the solid organ transplant may be chosen from a heart, a lung, a liver, a kidney, a pancreas, any combination of heart, lung, pancreas, liver and kidney. The organ may be obtained from a living donor or a deceased donor. The organ may be a whole organ or a part of an organ. For example liver transplants can involve the transplant of a whole liver, or a part of the liver.

Where the transplanted solid organ is a heart the method of the invention may be used to determine the patency of any vessel anastomosed to the heart, e.g. inferior vena cava, superior vena cava, atrial cuffs, aortic root, aorta and its branches (e.g., descending aorta, common carotid, subclavian), pulmonary trunk, pulmonary artery, pulmonary vein, or their combined anastomosis to the atrium. Where the transplanted solid organ is a lung the method of the invention may be used to determine the patency of any vessel anastomosed to the lung, e.g., pulmonary vein, pulmonary artery. Where the transplanted solid organ is a liver the method of the invention may be used to determine the patency of any vessel anastomosed to the liver, e.g., the hepatic artery, the heptatic vein, and branches of either, the portal vein, as well as, the bile duct and its branches. Where the transplanted solid organ is a kidney the method of the invention may be used to determine the patency of any vessel anastomosed to the kidney, e.g., the renal artery, the renal vein, the ureter. Where the transplanted solid organ is a pancreas the method of the invention may be used to determine the patency of any vessel anastomosed to the pancreas, e.g., the splenic artery and its branches, the pancreaticoduodenal arteries and its branches, the pancreatic duct. The vessel may be an arterial graft or venous graft in any of the solid organ transplants described herein.

Suitable fluorescent dyes include any non-toxic dye which fluoresces when exposed to radiant energy, e.g. light. In certain embodiments the dye is a fluorescent dye that emits light in the infra red spectrum. In certain embodiments the dye is a tricarbocyanine dye such as indocyanine green (ICG). In other embodiments the dye is selected from fluorescein isothiocyanate, rhodamine, phycoerythrin, phycocyanin, allophycocyanin, o-phthaldehyde, fluorescamine, Rose Bengal, trypan blue, and fluoro-gold. The aforementioned dyes may be mixed or combined in certain embodiments. In some embodiments dye analogs may be used. A dye analog includes a dye that has been chemically modified, but still retains its ability to fluoresce when exposed to radiant energy of an appropriate wavelength.

In some embodiments the dye may be administered intravenously, e.g., as a bolus injection. In some embodiments the bolus injection may comprise a volume of about 0.5 ml. In other embodiments the bolus injection may comprise a volume in the range of about 0.1 ml to about 10 ml. In some embodiments the dye may be injected into a vein or artery. In yet other embodiments the dye may be injected directly into the transplanted organ. In still other embodiments, the dye is injected within about a 15 cm radius of the transplanted organ. In yet other embodiments the dye may be administered parenterally. Where multiple dyes are used they may be administered simultaneously, e.g. in a single bolus, or sequentially, e.g. in separate boluses. In some embodiments the dye may be administered by a catheter, e.g. during a minimally invasive procedure.

The dye may be administered at a suitable concentration such that the fluorescence may be detected when the appropriate wavelength of radiant energy is applied. In some embodiments where the dye is ICG a suitable concentration is about 0.03 mg/ml at the site of detection. In other embodiments a suitable concentration of ICG is in the range of about 0.003 mg/ml to about 75 mg/ml. In some embodiments the ICG is administered in the range of about 1 mg/kg body weight to about 6 mg/kg body weight. In yet other embodiments the dye is administered at a concentration of about 0.5 mg/kg body weight. In still other embodiments the dye is administered in a range of about 0.01 mg/kg body weight to about 3 mg/kg body weight. In certain embodiments a suitable maximum daily dose of ICG may be administered to a subject. The maximum daily dose may be in the range of about 70 mg-about 140 mg.

The dye may be provided as a lyophilized powder or solid. In certain embodiments it may be provided in a vial, e.g. a sterile vial which may permit reconstitution with a sterile syringe. It may be reconstituted using any appropriate carrier or diluent. Examples of carriers and diluents are provided below. In certain embodiments the dye may be reconstituted at a concentration in the range of about 0.001 mg/ml-100 mg/ml. In other embodiments the dye is reconstituted to a concentration of about 10 mg/ml, about 20 mg/ml, about 30 mg/ml, about 40 mg/ml, about 50 mg/ml. The dye may be reconstituted, e.g., with water, immediately before administration.

In certain embodiments the dye may be administered to the subject less than an hour in advance of obtaining an image. In some embodiments the dye may be administered to the subject less than 30 minutes in advance of obtaining an image. In yet other embodiments the dye may be administered at least 30 seconds. In advance of obtaining an image. In still other embodiments the dye is administered contemporaneously with obtaining an image.

Diluents and Carriers

Any diluent or carrier which will maintain the dye in solution may be used. As an example, in certain embodiments where the dye is ICG the dye may be reconstituted with water. In other embodiments where the dye is ICG, the dye may be reconstituted with an alcohol, e.g., ethyl alcohol. In some embodiments once the dye is reconstituted it may be mixed with additional diluents and carriers. In some embodiments the dye may be conjugated to another molecule, e.g., a protein, a peptide, an amino acid, a synthetic polymer, or a sugar e.g., to enhance solubility or to enhance stability.

Additional examples of diluents and carriers which may be used in the invention include glycerin, polyethylene glycol, propylene glycol, polysorbate 80, Tweens, liposomes, amino acids, lecithin, dodecyl sulfate, phospholipids, deoxycholate, soybean oil, vegetable oil, safflower oil, sesame oil, peanut oil, cottonseed oil, sorbitol, acacia, aluminum monostearate, polyoxylethylated fatty acids, and mixtures thereof. Additional buffering agents may optionally be added including Tris, HCl, NaOH, phosphate buffer, HEPES.

Radiant Energy

In certain embodiments of the invention radiant energy is applied to the transplanted solid organ, or a vessel communicating directly, or indirectly with the solid transplanted organ, in an amount sufficient to cause a fluorescent dye to fluoresce thereby permitting at least one of the transplanted solid organ, or a vessel communicating directly, or indirectly with the solid transplanted organ to be imaged. In some embodiments the energy is light energy. In some embodiments the source of the light energy is a laser. An example of a suitable laser is the Magnum 3000 (Lasiris St-Laurent, Quebec, Canada), however, the skilled artisan will appreciate many other suitable lasers are commercially available. The laser may be comprised of a driver and diode. Preferably, the laser is a high power laser diode (HPLDs). Examples of HPLDs include AlInGaAsP lasers and GaAs lasers which are well known in the art. Such sources can be single diodes (single emitters), or diode-laser bars, which are made from edge emitting semiconductor chips. The laser may optionally include a filter, e.g. a bandpass filter, to ensure that the emitted radiation is of a substantially uniform wavelength. The laser may comprise optics for diverging the laser. The optics may be adjustable permitting variation in the field of illumination. The adjustable optics may also be used to provide even illumination over a given area.

In some embodiments the laser output is continuous or quasi continuous. In other embodiments the laser output is pulsed. The pulsed output may be synchronized with image acquisition by using a pulse generator. In some embodiments the laser pulse may last for at least 3 femtoseconds. In some embodiments the laser output lasts for about 30 seconds. In other embodiments the laser output lasts about 0.5 seconds-about 60 seconds. A suitable repetition rate for the pulsed laser may be in the range of e.g., 1 Hz-80 MHz, 10 Hz-100 Hz, 100 Hz-1 kHz, 1 kHz-100 kHz, 100 kHz-80 MHz. In some embodiments the laser may be operated at power output of 2.2 watts. In other embodiments the laser may be operated at power output in the range of 1-4 watts. In still other embodiments the average power is less than 5 watts.

In some embodiments the source of the light energy is an incandescent light with an appropriate filter so as to provide a suitable wavelength of light to induce the fluorescent dye to fluoresce. In yet other embodiments the light source is light emitting diode (LED).

In same embodiments the light energy may have a wavelength in the range of 150 nm-1500 nm. In other embodiments the light energy may be comprised of infra red light. In some embodiments the administered light has a wavelength of about 805 nm. In other embodiments the administered light has a wavelength in the range of about 805 nm-850 nm. The light energy may be administered at a wavelength which is shorter than the collection wavelength, i.e. detection wavelength. The light energy may be administered diffusely so as hot to damage the irradiated tissue. In some embodiments the light is administered over an area of about 7.5 cm×7.5 cm. In other embodiments the light is administered over an area in the range of about 1 cm×1 cm to about 20 cm×20 cm. As described above, multiple dyes may be used in some embodiments. In these embodiments, multiple light sources may be used, e.g., a first laser to excite a first dye and a second laser to excite the second dye. The skilled artisan will understand that the light source will be chosen or configured to excite a particular dye. In another embodiment single light source may be configured to excite multiple dyes, e.g., by alternating the wavelength at which energy is emitted.

Image Acquisition

Image acquisition may be achieved using any sensor capable of defecting a fluorescent signal. Examples include silicon based sensors, composite metal oxide semi oxide (CMOS) sensors and photographic film. In one embodiment the sensor comprises a camera, e.g. charge coupled device (CCD). Examples of a CCD include the Hitachi KP-M2; KP-M3 (Hitachi, Tokyo, Japan).

In certain embodiments an endoscope may be used, e.g., for interventional applications. It includes a sensor. The endoscope may additionally comprise a source of radiant energy. The endoscope may be comprised of optical fibers. In certain other embodiments a microscope comprising a sensor may be used, e.g., a surgical microscope. In another embodiment me sensor comprises a video camera. In certain embodiments the sensor may capture images at the rate of at least 10 per second, at least 15 per second, at least 20 per second, at least 30 per second, at least 50 per second. Thus in certain embodiments the invention contemplates a plurality of images. In other embodiments the invention contemplates one image.

The camera may be comprised of a means for focusing the image. In certain embodiments the invention contemplates a manual means for focusing an image. In other embodiments the invention contemplates an automated means for focusing an image. The camera may further be comprised of a lens system that permits magnification of an image field.

In one embodiment the relative positioning of the camera and laser is fixed so as to enhance clarity and minimize background noise. In this embodiment the laser is located at an angle of less than about 85° with respect to the axes of the laser and me camera. In another embodiment the laser is located at an angle from about 20° to about 70° with respect to the axes of the laser and the camera.

In certain embodiments the camera relays the captured image to an analog to digital converter and then through image capture and processing software running on a computer. The digital image of the fluorescing agent, corresponding to the transplanted organ and/or communicating vessel, may then be displayed on a monitor and recorded by the computer or a peripheral device. The image may be stored in any suitable medium, e.g., a hard drive, an optical disk, magnetic tape. The camera may also direct images to a television/VCR system such that the images may be displayed in real time, recorded and played back at a later time.

Systems of the Invention

In certain embodiments the invention provides a system for imaging at least one vessel joined to a transplanted solid organ, see, e.g., FIG. 1. The system may be used intra-operatively during transplant surgery to visualize at least one surgically exposed vessel which is joined to the transplanted organ.

System Overview

FIG. 1 illustrates an example of an electrical configuration of a system of the invention. In one embodiment, power supply 110 provides energy to thermo-electric cooler and controller 120, energy source 130 and controller/timing circuit 140. The controller 126 controls the temperature of energy source 130. For example, the temperature of a diode laser affects its operating wavelength, (e.g., a 0.3 nm shift per degree Celsius). In some embodiments, as described below, the energy source 130 may not be a diode laser, and hence a controller 120 may not be necessary. Controller/timing circuit 140 times the energy source 130 to the detector/camera 100 through computer 150. System computer 150 receives instructions from computer 150. It also includes image processing software on computer 150 readable medium. Computer 150 is in electrical communication with camera 100 and display 160. Display 160 receives image data from computer 150 and displays it. As described above, in some embodiments, the energy source 130 is a laser. It has a fiber 170 through which light energy is transmitted. Fiber 170 connects to illumination lens 180 through which light is illuminated when mechanical shutter 190 is open. An emission filter 210 may be used to filter light above or below the wavelengths at which the fluorescent dye is excited. In other embodiments, the energy source 130 may be an LED. It would directly illuminate the tissue of interest (i.e., no fiber 170 may be required.) The light energy irradiates a tissue of interest. Camera 100 captures radiation emitted by the dye after it is excited and transmits detected data to computer 150. The lens 180, fiber 170, and camera 100 are part of imaging head 230. The head 230 may be an articulating head. In some embodiments, head 230 further includes a distance sensor/focus indicator 220. The components of the systems of the invention are further described herein.

In certain embodiments, the system comprises: a) an energy source 130 capable of emitting sufficient energy such that the fluorescent dye fluoresces; and b) an imaging head 230. The system is configured for use with methods disclosed herein. In some embodiments, the system further includes one or more of: c) an articulating arm; e) a computer 230 and monitor; d) image processing software; e) an electrical power source; and f) a housing for containing a-f, wherein the housing is portable and comprises at least 2 wheels. In some embodiments the system may also comprise at least one of the following: a motion sensor; a distance sensor 220; a sterile drape; and a printer. The system may further comprise an instruction booklet. The system may be portable and thus may be transported in and out of the operating room. The system may be self standing and thus does not require to be held by a physician or a technician.

The imaging head 230 may be comprised of a sensor 220, e.g., a camera 100. The imaging head 230, may in some embodiments also contain the energy source 130, e.g. the laser. In some embodiments the laser contained within the imaging head 230 provides a nominal ocular hazard distance (NOHD) of about 27 cm. The NOHD is the distance at which the beam irradiance or radiant exposure equals the corneal maximum permissible exposure. In certain embodiments the imaging head 230 is joined to the housing by virtue of the articulating arm.

The articulated arm provides six degrees of freedom for the imaging head 230. The imaging head 230 can be translated and positioned in three linear movements (X, Y and Z), and three angular movements (pitch, yaw and roll). Pitch is the rotation of the imaging head 130 about the Y axis. Roll is the rotation of the SPY HEAD about the X axis and Yaw is the rotation of the SPY HEAD about the Z axis.

The articulated arm is comprised of three sections, the horizontal section, the articulated section and the yoke. The horizontal section attaches to the cart, or housing, and provides movement along the horizontal axis (X axis and also roll) and can move in 270 degrees of freedom. The articulated section is hinged in the middle of its length forming two segments. Each segment can rotate with 90 degrees of freedom in one axis. The articulated section provides movement in the vertical axis (Z and also X and Y). The yoke section is a curved section that attaches to the distal end of the articulated section. The yoke has two rotational attachment points. One point attaches to the articulated arm and the other to the imaging head 230. The yoke provides the imaging head 230 two rotational degrees of freedom (pitch and roll). The articulating arm thus provides a means for positioning the imaging head 230 directly over the subject.

In certain embodiments the imaging head 230 is positioned above the patient and the appropriate field of view is obtained with the aid of real time images on a computer 150 monitor. The physician may adjust the range of focus, e.g., by intermittently observing images on the computer 150 monitor. In another embodiment two laser pointers are provided, e.g., one at each end of the imaging head 230. The laser beams may radiate green light. The laser beams from the pointers point down toward the patient and provide a means of focusing the camera 100, without the need to look away from the patient, e.g., at a computer 150 screen. When the two dots from the laser beams converge the centre of the image is determined. The device may be provided with buttons that allow for manually turning the laser pointers on end off. The buttons may be covered by the sterile drape, but may protrude enough to facilitate ease in switching the laser pointers on and off.

In certain embodiments the computer 150 is a personal computer comprising at least 512 Megabytes of random access memory (RAM) and at least 10 Gigabytes of storage. In some embodiments the computer 150 may contain a Pentium IV processor (Intel, Santa Clara, Calif.). In some embodiments the computer 150 may also have a CD and DVD drive. The drive may have read and write functionality. The system also provides image processing software.

Figure 2:
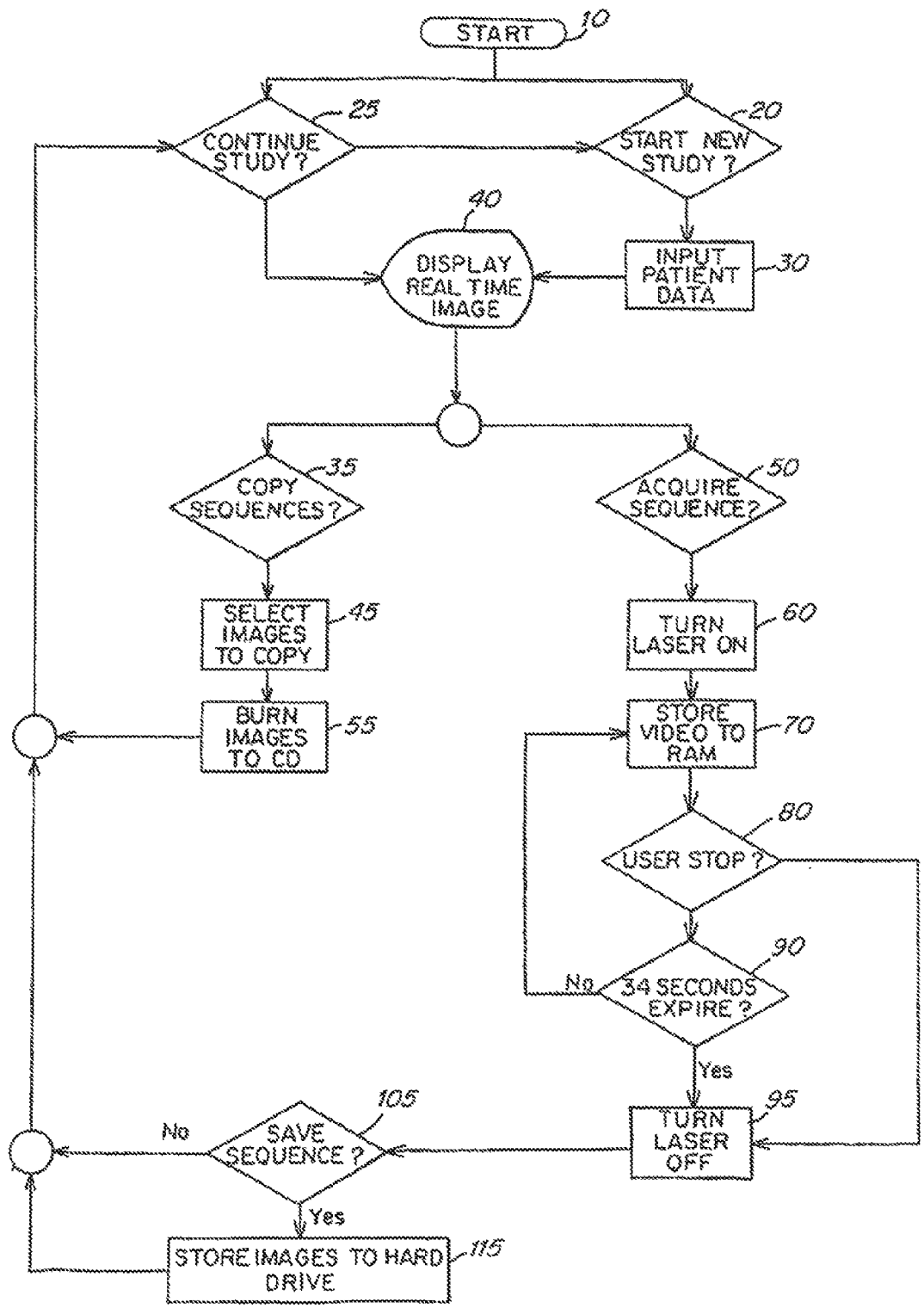
FIG. 2 illustrates imaging software that may be used in certain embodiments of the invention.

FIG. 2 illustrates a flowchart of software that may be used within the scope of the present invention. The skilled artisan will understand that such software includes instructions stored on computer-readable medium. When executed, the software program provides instructions to the computer processor as described below. The skilled artisan will further understand that the computer is in communication with the laser, sensor and display as described herein.

At start (step 10) the user may be presented with multiple dialog boxes or other common user interface paradigms. For example, the user may be queried about whether he wishes to start a new study (step 20). If the user indicates that he does, he may be instructed to input or otherwise select a patient for the study. For example, the user may be prompted to choose a name from a list linked to a database that is accessible to the computer. Alternately, he may be prompted to input a patient identifier. The computer may then access the database to determine the existence of additional information associated with the patient, and preferably to obtain such information. In a preferred embodiment, the software requires the user to input or otherwise select values for Patient First Name, Last Name and ID number fields. Most preferably, sufficient information is inputted or otherwise loaded so that images may be stored according to the Digital Imaging and Communications in Medicine (DICOM) standard. The DICOM Standard is a product of the DICOM Standards Committee and its many international working groups. Day-to-day operations are managed by the National Electrical Manufacturers Association (Rosslyn, Va.). The standard is publicly available at the website http://medical.nema.org/, and is incorporated herein by reference in its entirety.

After patient data is inputted, the monitor or other display displays images captured by the camera or other sensor in communication with the computer (step 40). At this point, the user can change the position, orientation, gain or other parameter of the camera to obtain a desired view of the patient.

Alternately, the user may choose to continue a study (step 25) at start 10. Upon such indication, the process proceeds to step 40.

Once the image is displayed, the user is prompted to indicate whether he wishes to copy sequences (step 35) or acquire sequence (step 50). The term "sequences" refers to data associated with real-time images captured by a camera or other sensor in communication with the computer. Once the user indicates that he wants to acquire images from the sensor in step 50, the computer causes the laser to turn on, and it stores the video sequence obtained from the sensor in RAM (step 70). Real time images continue to be displayed on the display. The user is then queried about whether he wishes to turn the laser off (step 80). If he indicates that he does, the computer causes the laser to shut off (step 100). Alternately, if the user does not indicate that he wants to shut off the laser, the computer determines whether a pre-determined amount of time (e.g., 34 seconds) has elapsed from step 60. Once that pre-determined amount of time has elapsed, the computer causes the laser to shut off. The video sequences continue to be stored in RAM until the laser is turned off. Once the laser is turned off, the user is queried as to whether he wishes to save the sequence (step 110). If he indicates in the affirmative, then the sequences are stored to hard drive (step 120) or other media.

Returning now to step 40 for purposes of describing the software, once the real time image is displayed, the user is queried as to whether he wishes to copy sequences (step 35). If the user indicates that he does, the images associated with the study are selected and burned on compact disk or other selected media (step 55). Alternately, the software may allow the user to select specific images for storage on selected media. Preferably, the image(s) are stored in a format that is compatible with a picture archiving and computer system, for example in a DICOM format.

In another embodiment, the camera may also direct images to a television/VCR system such that the image(s) may be displayed in real time and/or recorded and played back at a later time. Since the image(s) may be used to guide all or part of the surgical procedure, the image(s) may be displayed through out the length of the surgical procedure. In other embodiments, the image(s) may be displayed for less than the entire length of the surgical procedure. In another embodiment the software permits manipulating the images after acquisition, such as zooming, region of interest selection, change of brightness and contrast, and displaying multiple images simultaneously.

In certain embodiments the image processing software permits selection of the optimal image for analysis. In some embodiments the image processing software may permit manipulation of contrast. In some embodiments the image processing software can permit manipulation of resolution. In another embodiment the image processing software can permit manipulation of the number of pixels in a field. In another embodiment the image processing software may permit control of the rate at which images are acquired. The software may be able to determine the relative contrast of one image with another, and thus select the images having the greatest contrast for analysis, e.g., images of transplanted organs emitting detectable fluorescence.

In certain embodiments software on computer readable media may be used to compare images of pre and post treatment vessels to determine flow within the vessel, e.g., blood flow, or used to compare pre and post tissues to determine change in tissue perfusion. A change in fluid flow through one or more vessels would be determined where the first and second images are fluorescent images of vessels, e.g., blood vessels. A change in tissue perfusion would be determined where the first and second images are fluorescent images of tissue. In certain embodiments, the software includes an algorithm, e.g., pixel detection algorithm. In certain embodiments, the software includes instructions for determining the pixel intensities or brightness of two registered images, e.g., by a pixel detection algorithm, and further includes instructions for determining the change in pixel intensities between the two images. For example, a difference may be determined by subtracting the intensity of a first pixel in the first image from a second pixel in the second image. In some embodiments, the mean, median or mode difference is determined for some or all pixels in the two images. In some embodiments, the two images are registered and correspond to the same or approximately same space or portion of the body part being imaged. In another embodiment, a global pixel intensity value, such as mean, mode, or median pixel intensity is calculated for each of the images and the difference in the two values is determined. In yet another embodiment, more than two images may be taken, and the difference in individual, mean, mode, or median pixel intensity may be determined over time. An increase in intensity in pixels pre to post treatment indicates greater perfusion in tissue or fluid flow through vessels, while a decrease may indicate a decrease in perfusion in tissue or flow through vessels. In another embodiment, the software includes instructions for determining the number of pixels in two or more images that are indicative of fluorescence and determining the difference between these determined numbers. In some embodiments, the difference is determined as a function over time. An increase in the number of pixels indicative of fluorescence is indicative of an increase or greater patency or flow, while a decrease suggests less patency or flow.

In some embodiments, the two or more images are registered. For example, a solid state accelerometer is used to determine position of the imaging head with respect to normal (earth's gravity). The accelerometer measures acceleration typically in units of meters/second squared. The steady state signal or DC value of this signal can be used to determine inclination with respect to vertical. The derivative with respect to time of the accelerometer signal may be used to determine velocity of the imaging head. The skilled artisan is familiar with other registering techniques.

Thus, in one embodiment, the invention provides a method for determining the success of a treatment in a subject who has been administered a fluorescent dye as described herein. The method includes the steps of (a) obtaining a first fluorescent image before a treatment, (b) obtaining a second fluorescent image after the treatment, and (c) comparing the change in fluorescence between the first and second image to determine whether the treatment has resulted in a greater or lesser tissue perfusion or fluid flow in a vessel. In some embodiments, pixel intensity may be compared between more than two images. In some embodiments, the pixel intensity may be the mean, mode, or median pixel intensity of pixels in an entire image part of an image. In certain embodiments, the effect of lesion or anti-tumor therapy can be determined by determining whether there is a decrease in pixel intensity wherein a decrease in pixel intensity is indicative of a decrease in perfusion or blood flow.

Examples of treatment may include anti-cancer drugs, surgical bypass, open heart surgery, or any other therapeutic regimen that is expected to result in an increase or decrease in tissue perfusion or blood flow in an area of interest.

The system also provides, in certain embodiments, a housing to contain the computer, the monitor, the electrical supply, the printer, and the imaging head. The housing may be portable to permit movement within the operating room or alternatively to permit movement of the system in and out of the operating room. In some embodiments the housing is comprised of at least two wheels. In other embodiments the housing is comprised of four wheels. The wheels may have locks to prevent unwanted movement.

In certain embodiments the housing has a width of about 30 inches, a depth of about 35 inches and height of about 82 inches. In certain embodiments the housing width is less than 45 inches. In certain embodiments the depth is less than 45 inches. In certain embodiments the height is less than 102 inches. The housing is not hand held, and thus the system is not required to be hand held.

The electrical power supply may be comprised of a lock in some embodiments. The lock serves as a safety device to prevent inadvertent activation of the system, in particular activation of the laser.

In some embodiments the system may be comprised of a motion detector. The motion detector determines if the imaging head moves. In certain embodiments the system comprises a distance sensor. The distance sensor determines the distance between the imaging head and another object, e.g. the subject in some embodiments it incorporates a visual display which provides feedback to a physician so that the laser and camera may be located at a distance from the tissue of interest that is optimal for capturing high quality images, thereby minimizing the need for focusing the camera during the procedure. The motion sensor and distance sensor may each be located on the imaging head, for example.

In some embodiments the system comprises a sterile drape. The sterile drape covers the articulating arm to prevent or minimize the risk of contamination of the subject. The sterile drape may have an aperture in it. The aperture may be covered with a material which is capable of transmitting radiant energy, e.g., infra red light generated by a laser.

Apparatus

Certain embodiments of the invention provide an apparatus which may be used for intra-operative imaging, e.g., in a surgical suite. The apparatus may be portable so that it may be conveniently transported into and out of an operating room. The apparatus may be free standing and thus not require a physician, nurse or technician to hold it. The apparatus may include one or more systems of the invention. In some embodiments the apparatus may also comprise at least one of the following: a motion sensor; a distance sensor; a sterile drape; and a printer. In some embodiments the housing is comprised of at least two wheels. In other embodiments the housing is comprised of four wheels. The wheels may have locks to prevent unwanted movement. The apparatus may also comprise a focusing device, e.g., at least one focusing laser, e.g. a first and a second laser pointer, the first laser pointer positioned at a first end of the imaging head, and a second laser pointer positioned at a second end of the imaging head. The two laser pointers may be provide radiant light in the green wavelength range and may provide a means of focusing the camera.

The apparatus may be of a suitable size so that it is free standing, but is small enough so as not to provide a significant obstruction in an operating room. In certain embodiments the apparatus has a width of about 30 inches, a depth of about 35 inches and height of about 82 inches. In certain embodiments the apparatus width is less than 45 inches. In certain embodiments the apparatus depth is less than 45 inches. In certain embodiments the apparatus height is less than 102 inches.

Example 1

This example illustrates a system of the invention. The imaging devices is made primarily of few subsystems that are primarily optical in nature, an illumination subsystem and a detection subsystem. Other subsystems are primarily electrical or mechanical in nature. The illumination subsystem includes a fiber-coupled, infrared laser, a light guide, and a projector lens. The detection subsystem includes a high-quality imaging lens, a narrow band-pass filter, and a CCD camera. The remainder of the system includes a laser, video display, computer and other auxiliary control circuits. The system is designed with an articulated arm with an imaging head. The imaging head contains the imaging and illumination optics and electronics. The articulated arm allows the illumination and imaging systems to be positioned over the field of operation.

Mounted inside this imaging head are the filter and CCD camera, a distance sensor and the light guide and projection lens. A power delivery optical fiber is routed through the articulated arm connecting the laser to the light guide in a low-loss manner.

Illumination Subsystem

A fiber-coupled diode laser with a nominal 2 W output is used as a light source. Wavelength is specified to be 806 nm, which can be reached through use of a thermo-electric cooler attached to the laser mechanical package. For the nominally 30% efficient laser, a heat load of about 7 W would be offered to the surrounding mechanical structure. The temperature of a diode laser affects its operating wavelength, typically 0.3 nm shift per degree C. Additionally, diode lasers have a maximum operating temperature that must never be exceeded. These factors make a temperature control circuit not merely good engineering practice, but also an environmental requirement to achieve long lifetimes (10,000+ hours).

Since modern diode laser manufacturing practice cannot tightly control the power vs. current characteristic, each diode is different, and the maximum power for each unit will be different. The assembly and calibration procedure will individually set the operating current for each unit differently. Since a requirement of the system is to deliver a fixed amount of power to the patient (2.0 W nominal), the illumination subsystem will be designed with a high enough efficiency to guarantee an excess of power delivered when the laser is run at maximum current. During final calibration of the system, the laser diode current will be decreased from maximum to reach the 2.0 W requirements.

The output spectrum of most diode lasers is not "line-like" as in an ideal laser. The spectrum extends over several nm and usually shows prominent peaks. There is also a broad (several 10's of nm wide) low-level pedestal of power. For most fluorescence excitation applications, the broad spectral output of these high-power laser diodes requires an external excitation filter to prevent overlapping of the laser light with the emission band. Prototype experiments performed have shown that this extra filter is not required to achieve a good signal-to-noise ratio in the detected fluorescent image.

Power Delivery Fiber

The system uses a fiber optic cable to carry to the optical power from the laser diode to the optics. The laser's fiber is a multimode fiber, whose core can support many modes of laser transmission. This transfers power without burning the fiber. The core diameter (which sets the effective emitting area) is about 200 microns. The spatial pattern of light emitting from the fiber end is approximately a top hat (with rounded corners) in angle. The output is characterized by the fiber Numerical Aperture (NA) which is the sine of the half angle corresponding to the HWHM. A typical power delivery fiber would have an output NA=0.15, corresponding to a FWHM of about 17°.

Light Guide

To project a square illumination pattern of roughly 76×76 mm the light from the fiber is coupled to a light guide with a square cross section. The light guide may be made of any number of acceptable glasses (e.g. BK7). Note that some optical glasses (e.g. Pyrex) or clear plastics (e.g. polycarbonate) have a large bubble density or high refractive index inhomogeneity. This can lead to significant extraneous losses. The approximate dimensions are 0.25×0.25×4.00 inches. All faces should be polished to approximately 50/80 scratch/dig and flat to within about 5 waves. Protective chamfers (usually a good idea) are to be avoided here since they also can lead to significant extraneous losses.

The purpose of the light guide is to homogenize the laser light. The coupling from the fiber is simply an air gap of a few millimeters. The only requirement is that the end-face of the light guide capture all of the emitted cone of light from the fiber. Thus, for 0.22 NA fiber, the fiber is positioned no further away than 14 mm.

The operation of the light guide is now described. At each point on the exit face, the total laser field is the sum of several fields, some of which have undergone one or more total internal reflections. If scattering losses are kept low, the total power reaching the exit face equals the input power from the fiber, minus Fresnel losses at the end-faces. The radiant distribution is no longer a cone emitted from a small fiber core, but a homogenized, square emitter, with maximum angle equal to the fiber cone angle. Homogeneity improves with length of the light guide. Non-sequential ray-tracing calculations show uniformity with about 20% falloff at the edges after only 4 inches of guide. This is not a diffuse emitter, since for each point on the end-face there are certain definite angles of emission.

Mechanical Interface

The light guide has only a mechanical interface. Preferably, the light guide entry face needs to be within 14 mm of the power delivery fiber exit ferrule. If the cone of light is tight enough, the groove can have a depth of 1 mm without significantly attenuating the light.

The entry face is furthermore tilted with respect to the long axis of the light guide. This allows mechanical access to the Fresnel-reflected beam. A photodiode is placed within this "stray" beam as a power monitoring device. A tilt angle of 20° is arbitrarily chosen as a compromise. The larger the angle, the easier it is for photodiode access and space for fiber connector. The smaller the angle, the easier to manufacture without edge chips and the more robust the overall unit. Optically, coatings can minimize the reflection for just about any angle, but for steep angles of incidence, there can be a great difference in the reflection coefficients for the two orthogonal polarizations. It's best to keep the difference small and use near-normal incidence angles.

Projection Lens

To project the object of square-faced emitter to the region of interest about 30 cm away, a simple two-element air-spaced condenser lens is used. Since we want to create an illuminated region of 76.2×76.2 mm from a 6.35×6.35 mm emitter, we need a magnification of 12.0×. This defines the ratio of image to object distance. For 320 mm (allowing some mechanical clearance for packaging), the required object distance is 26.7 mm. This corresponds to using a lens with a focal length of about 25 mm. The positional tolerance here is approximately ±0.5 mm.

Power Monitor

A photodiode and preamp circuit is included in the illumination subsystem to monitor the power being transmitted to the patent. The photodiode will be observing a small amount of light reflecting from the input face of the light guide. Without an anti-reflective coating, we expect about 4% of the total to be reflected, the usual Fresnel reflection, valid for small angles. To accommodate the reflected lights either the input face will be tilted slightly with respect to the axis of the light guide, or the fiber output will couple to the input face at a shallow angle.

The Fresnel reflections at both exit and entry faces can be either measured or calculated. The transmission of the condenser lens can be either measured or calculated. These characteristics that affect the total power delivered to the patient are quantities which do not change in time. It is a simple matter to generate a linear equation of power delivered to patient versus monitor photocurrent.

Detection Subsystem/Emission Filter

The infrared light from the laser at 806 nm excites fluorescence indocyanine green, which has been injected into the subject's bloodstream. The dye emits fluorescence at a peak wavelength of 830 nm. An emission filter is used to block the scattered laser light and pass the fluorescent light. Hence the filter is a bandpass filter.

The bandpass filter characteristics are a pass band centered at 830±5 nm and a 10 nm FWHM. It has a minimum attenuation in the stop band of OD 4.

The filter blocks the excitation laser light and the ambient light too. Hence, the device may be used in a brightly illuminated operating room.

Imaging Lens

The imaging lens is a commercial quality photographic lens with a male C-mount thread for attachment to the flange on the camera. The speed should be as fast as possible to collect the fluorescent light with the greatest efficiency. An initial specification is one which is commonly available in a variety of focal lengths—f/1.4. The CCD camera contains a CCD image sensor which is 6.45×4.84 mm (½ inch format). With a 16 mm focal length lens (commonly available focal length), the sensor "sees" a field of 122×92 mm, just over the required 75×75 mm.

CCD Camera

The CCD camera used is a commercially available unit from Hitachi. The KP-M2R has a spectral response that peaks at 640 nm and is useful in the NIR. Electrical power requirement is 12 VDC at 180 mA. Video output is via RS-170 on a standard BNC mount.

Specification of Laser Class.

To determine the laser class, use 21 CFR 1040.10 as the governing document. We start with a nominal 3 W laser output from the square 6.35×6.35 mm emitter. This radiation is inaccessible during normal operation. It passes through a projection lens to be focused to an image about 300 mm away. It is accessible during normal operation immediately after this lens.

The power through an aperture needs to be known to determine laser class. This will be accomplished by estimating the radiance of the final emitting surface (outer projection lens surface) and calculating the radiant transfer integral. The final surface of the light guide, while not truly diffuse, nonetheless approximates a uniformly emitting area; i.e. the power per small unit area is constant over the area of the emitter. Additionally, the emission is bounded in angle space; very little light is emitted at an angle greater that (corresponding to the input fiber NA of 0.15).

A good approximation to the radiance (power per unit area per steradian) can be calculated this way. The total power from the fiber endface is 3 W. There will be approximately the same amount at the final condenser lens surface, assuming the use of good AR coatings on all surfaces. The area covered by the light on the final condenser surface is a square of about 13 mm on a side. Since the spacing from the light guide endface to the final condenser surface is 33.6 mm, simple geometry would give 16.5 mm using the 8.6° emission angle. The refraction at the first lens in the condenser makes this a bit smaller. A ZEMAX™ ray-trace calculation which includes the full refractive effects of all lens surfaces yields 13 mm. The emitting area is 1.69 cm$^2$. Since this lens projects an image 75×73 mm at 300 mm away, the new maximum emission angle is 5.9°, corresponding to a new solid angle of 33.3×10⁻³ sr. Dividing the power by the area and the solid angle gives L=53.3 W/cm² sr.

The radiant transfer of power Φ from a source (subscript s) to a detector (subscript d) is $$\Phi = \int\int \frac{L\cos\theta_s \cos\theta_d}{s_{sd}^2} dA_s dA_d$$

where θ is the angle from the surface normal and s is the distance between the source and detector. The integrals are over the areas of the source and detector. The integral can be performed under the constraint of a circular source and a circular detector, the centers of which are both on axis. The result is $$\Phi = \frac{2L(\pi r_s r_d)^2}{r_s^2 + r_d^2 + s_{sd}^2 + \sqrt{(r_s^2 + r_d^2 + s_{sd}^2)^2 - 4r_s^2 r_d^2}}$$

In this case, the specification calls for $r_d$=0.35 cm (corresponding to a 7 mm diameter aperture) and $s_{sd}$=20 cm (to maintain the 10⁻³ sr solid acceptance angle). The source radius is 0.65 cm. Since $s_{sd}$ is much bigger than either $r_s$ or $r_d$, we may approximate the result as $$\Phi = \frac{L(\pi r_s r_d)^2}{s_{sd}^2}$$

Evaluating this expression numerically gives 68.1 mW at the detector. A bit of a subtlety in the previous calculation is that the source radius is 0.65 cm. But the emitting area is closer to a square with side of 1.3 cm. However, the approximation is good since the corners of the square are much less bright than the center. The true illumination pattern away from the exit face of the light guide is more cross-shaped than square. This laser illumination system falls well within Class IIIb specifications.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims.

What is claimed is:

1. A method of determining the patency of at least one vessel which is attached to a donor organ in a donor subject comprising:
   a. administering a fluorescent dye to the donor subject;
   b. applying energy to the vessel such that the fluorescent dye fluoresces;
   c. obtaining a fluorescent image of the vessel attached to a donor organ; and
   d. observing the image to determine if a fluorescent signal is continuous through the vessel,
   wherein a continuous fluorescent signal in the vessel indicates the vessel is patent, and wherein the fluorescent dye is a tricarbocyanine dye, fluorescein isothiocyanate, rhodamine, phycoerythrin, phycocyanin, allophycocyanin, o-phthaldehyde, fluorescamine, Rose Bengal, trypan blue, fluoro-gold, or a combination thereof.

2. A method of determining the patency of a donor organ comprising:
   a. administering a fluorescent dye to the vessel attached to the donor organ;
   b. applying energy to the vessel such that the fluorescent dye fluoresces;
   c. obtaining a fluorescent image of the donor organ; and
   d. observing the image to determine if a fluorescent signal is continuous through the donor organ,
   wherein continuous fluorescent signal in the donor organ indicates the donor organ is patent, and wherein the fluorescent dye is a tricarbocyanine dye, fluorescein isothiocyanate, rhodamine, phycoerythrin, phycocyanin, allophycocyanin, o-phthaldehyde, fluorescamine, Rose Bengal, trypan blue, fluoro-gold, or a combination thereof.

3. The method of claim 1, wherein the donor organ is a heart, a lung, a liver, a kidney, or a pancreas.

4. The method of claim 1, wherein the fluorescent dye is administered as a bolus injection.

5. The method of claim 1, wherein the tricarbocyanine dye is indocyanine green.

6. The method of claim 1, wherein the energy is provided by a laser.

7. The method of claim 1, wherein the energy is provided by a light emitting diode.

8. The method of claim 1, wherein the energy comprises infrared light.

9. The method of claim 1, wherein the fluorescent image is obtained with a surgical microscope or an endoscope.

10. The method of claim 1, wherein the image is obtained by a charge coupled device.

11. The method of claim 1, wherein the image is obtained by a video camera.

12. The method of claim 2, wherein the donor organ is a heart, a lung, a liver, a kidney, or a pancreas.

13. The method of claim 2, wherein the fluorescent dye is administered as a bolus injection.

14. The method of claim 2, wherein the tricarbocyanine dye is indocyanine green.

15. The method of claim 2, wherein the energy is provided by a laser.

16. The method of claim 2, wherein the energy is provided by a light emitting diode.

17. The method of claim 2, wherein the energy comprises infrared light.

18. The method of claim 2, wherein the fluorescent image is obtained with a surgical microscope or an endoscope.

19. The method of claim 2, wherein the image is obtained by a charge coupled device.

20. The method of claim 2, wherein the image is obtained by a video camera.

* * * * *